United States Patent [19]

Lewis et al.

[11] Patent Number: 5,217,013
[45] Date of Patent: Jun. 8, 1993

[54] PATIENT SENSOR FOR OPTICAL CEREBRAL OXIMETER AND THE LIKE

[75] Inventors: Gary D. Lewis, St. Clair Shores; Peter H. Klose, Clawson; Wayne P. Messing, Troy, all of Mich.

[73] Assignee: Somanetics Corporation, Troy, Mich.

[21] Appl. No.: 711,452

[22] Filed: Jun. 6, 1991

Related U.S. Application Data

[63] Continuation-in-part of Ser. No. 329,945, Mar. 29, 1989, Pat. No. 5,139,025, which is a continuation-in-part of Ser. No. 827,526, Feb. 10, 1986, Pat. No. 5,140,989, and a continuation-in-part of Ser. No. 542,022, Oct. 14, 1983, Pat. No. 4,570,638.

[51] Int. Cl.$^5$ ............................................. A61B 5/00
[52] U.S. Cl. ........................................ 128/633; 128/666; 356/41
[58] Field of Search ............................ 128/664-666, 128/633-634; 356/40, 41

[56] References Cited

U.S. PATENT DOCUMENTS

| | | | |
|---|---|---|---|
| 4,321,930 | 3/1982 | Jobsis et al. | 128/633 |
| 4,380,240 | 4/1983 | Jobsis et al. | 128/633 |
| 4,510,938 | 4/1985 | Jobsis et al. | 128/633 |
| 4,819,752 | 4/1989 | Zelin | 128/633 |
| 4,825,879 | 5/1987 | Tan et al. | 128/633 |
| 4,865,038 | 9/1989 | Rich et al. | 128/633 |
| 4,880,304 | 11/1989 | Jaeb et al. | 128/633 |
| 4,928,691 | 5/1990 | Nicolson et al. | 128/666 |
| 4,964,408 | 10/1990 | Hink et al. | 128/633 |
| 5,094,240 | 3/1992 | Muz | 128/666 |
| 5,111,817 | 5/1992 | Clark et al. | 128/666 |

FOREIGN PATENT DOCUMENTS

89/09566 10/1989 World Int. Prop. O. .......... 128/633

*Primary Examiner*—William E. Kamm
*Assistant Examiner*—Robert L. Nasser, Jr.
*Attorney, Agent, or Firm*—Price Heneveld Cooper DeWitt & Litton

[57] ABSTRACT

A sensor for use in medical patient examination and monitoring by spectrophotometric apparatus, including a main body having a soft, resilient outer cover on at least one side for conformably contacting a selected area on the patient, in particular the forehead, also having and an electro-optical light source and a plurality of electro-optical light detectors spaced from the source and from one another, and exposed to the selected site on the patient by light-transmissive passages extending through the resilient cover, in which the resilient cover is formed of a thin, softly compressible member of light-absorbing and moisture-transmissible material, preferably of resilient cellular polymeric foam.

18 Claims, 2 Drawing Sheets

PATIENT SENSOR FOR OPTICAL CEREBRAL OXIMETER AND THE LIKE

CROSS REFERENCE TO RELATED CASES

This patent application is related to and constitutes a continuation-in-part of copending application Ser. No. 329,945, filed Mar. 29, 1989, now U.S. Pat. No. 5,139,025, which in turn is related to and a continuation-in-part of prior applications Ser. Nos. 827,526, filed Feb. 10, 1986, now U.S. Pat. No. 5,140,989, and 542,022, filed Oct. 14, 1983, (now U.S. Pat. No. 4,570,638), and this application is also related to copending application Ser. No. 07/711,147. The disclosure of each such application is incorporated herein by reference.

TECHNICAL FIELD

This invention relates to optical spectrophotometric methods and apparatus, particularly as adapted for use in clinical in vivo procedures involving human patients; more particularly, the invention relates to a patient monitoring device and optical component carrier, preferably in the form of a headpiece, for use on the patient as the patient-spectrophotometer interface, by which optical-response spectrophotometric patient examination data is obtained.

BACKGROUND

In the above-referenced related prior patents, optical spectrophotometric procedures and apparatus are disclosed and described for in vivo clinical application to human patients, as well as a potential broader range of subjects, by which important biomedical information may be obtained which is directly indicative of intrinsic, internal biological and physiological processes, conditions, tissue or substance composition or state, etc., and these prior patents generally contemplate use of certain "optical probes", i.e., optical component mounting and carrying apparatus, by which the selected light wavelengths are emitted and administered to the patient and resulting light is detected and monitored at various positions and points on the patient.

While a principle focus of these prior patents is the use of such spectrophotometric techniques on human anatomy in a manner by which the relative spacing of the light-emitting and light-detecting elements was variable, the underlying significance of such spacing was the important consideration in this regard, and thus the disclosures in these patents also contemplate comparable or analogous sender-receiver configurations of fixed geometry. These concepts and considerations are the further subject of copending patent application Ser. No. 329,945 (filed Mar. 29, 1989), which in some respects is more particularly directed to the use of such optical spectrophotometric procedures on the human head, for and in conjunction with examination of certain parameters and attributes of brain condition and function. Accordingly, this last-mentioned copending application discloses and describes additional and other such "optical probe" or optical sensor patient interface configurations and devices which are particularly intended for (but not necessarily limited to) use on the human skull, for monitoring internal brain tissue and function through representative parameters.

The applicability and value of using such optical spectrophotometric procedures on an in vivo basis with human patients continues to gain credence and recognition, as well as wider understanding, with increasing development and progress. One development evidencing such further progress is disclosed in my copending application Ser. No. 07/711,147, filed Jun. 6, 1991, entitled: "Optical Cerebral Oximeter", in which apparatus and methodology is disclosed for implementing an optical spectrophotometric device for use in monitoring oxidative metabolism in the human brain and providing a readout directly in terms of percent hemoglobin oxygen saturation. The present invention is directed to a preferred form of patient headpiece for use in such device, as well as for potential use in other analogous such devices, providing a further advanced and improved "optical probe" or patient-machine interface, by which optical-response data is obtained from the patient and supplied to a spectrophotometric device.

Prior participants in the art have addressed similar underlying considerations, and reference is particularly made to the work of Frans F. Jobsis et al, as represented in and by prior U.S. Pat. Nos. 4,223,680; 4,281,645; 4,321,930; 4,380,240; 4,510,938; and 4,805,623. While certain of the underlying concepts and/or scientific assumptions or theories set forth in these patents differ from those addressed by the present inventor, as reflected by the related and referenced prior and copending patents and applications identified above, these prior patents attributed to Jobsis et al contain considerable information, etc. of interest to the general subject matter hereof, and certain such patents (in particular, U.S. Pat. Nos. 4,321,930, 4,380,240 and 4,510,938) expressly disclose patient headpieces for use in generally similar in vivo optical spectrophotometric procedures. Accordingly, these and other such prior teachings provide background information of definite interest, and to some extent this may be said in connection with various embodiments of arterial pulse oximeters patented previously and in common use; for example, see U.S. Pat. Nos. 4,013,067, which shows a flexible strap-like device for carrying optical senders and receivers, adapted for encircling the finger of the patient and thus accessing arterial blood vessels therewithin.

BRIEF SUMMARY OF INVENTION

As indicated above, the present invention provides improvements in optical spectrophotometric sensor assemblies, i.e., "optical probes", particularly adapted for in vivo use as the patient interface in clinical spectrophotometric patient-monitoring apparatus such as the aforementioned cerebral oximeter disclosed in copending application Ser. No. 329,945.

Accordingly, the major objectives of the invention, and the advantages attributable thereto, comprise the provision of a new and improved form of patient headpiece for obtaining optical spectrophotometric data on an in vivo basis in clinical use, and the improved apparatus in accordance with the invention includes both general and particular features and attributes of such a device, comprising generally a flexible support or component-carrier adapted for comfortably conforming to the shape of the patient's cerebrum or other such anatomical area, with particular component-mounting structure and apparatus for optimizing the introduction of the selected light spectra into a selected internal tissue volume or region of examination, as well as for enhancing the faithful and accurate detection of the low-level resulting light and corresponding signals produced and processed to obtain the desired biomedical information.

In a more particular sense, the invention provides an improved form of such headpiece, together with particular preferred componentry, including optical (light-emitting and detecting) components as well as particular preferred mounting structure and arrangements therefor within the soft, comparatively flexible support or carrier. In addition, a preferred form of electrical circuitry is provided for the device and its light-emitting and light-detecting components, together with novel shielding therefor to protect against contamination of the electrical signals representative of the optical data by ambient electromagnetic or electrostatic fields, etc.

In addition, the invention provides novel structural and mounting (securement) means for the electro-optical components as noted above, and further includes means for shielding the same from optical disruption or contamination during use in the anticipated environment, to thereby further enhance the fidelity of the optical response obtained, and the entire apparatus as disclosed is conducive to manufacture as a disposable, single-use component which lends itself readily to customary and familiar clinical sterilization techniques, and is also adapted for rapid connection and disconnection to the spectrophotometric control and processing unit.

The foregoing major objectives, advantages and considerations of the invention, together with and including others, will become more apparent following consideration of the ensuing specification, particularly taken in conjunction with the appended drawings, briefly described hereinafter. Once again it is pointed out that the apparatus and methodology principally described hereinafter constitutes merely a preferred embodiment of the underlying invention, and does not specifically address other and further aspects thereof which will or may become further appreciated by those skilled in the art after consideration of the overall disclosure herein.

DESCRIPTION OF PREFERRED EMBODIMENTS

Figure 1:
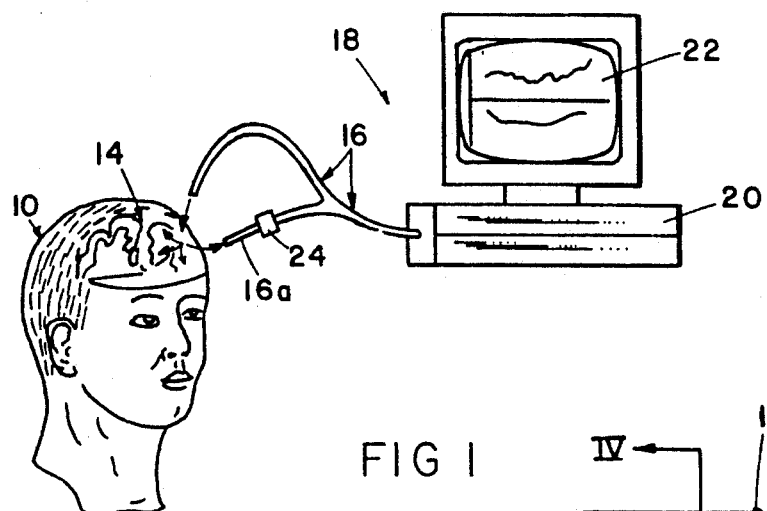
FIG. 1 is a schematic pictorial representation showing a typical operative environment for the apparatus in accordance with the invention, including representative elements thereof.

FIG. 1 comprises a representative and pictorial showing of a typical clinical setting in which optical spectrophotometric apparatus in accordance with the invention is to be used, as part of an operative system for monitoring or examining patients. In fact, FIG. 1 is taken directly from the aforementioned copending application Ser. No. 07/711,147, which describes the overall cerebral oximeter system in considerable detail. For purposes of the present disclosure, it need only be said that FIG. 1 shows a human patient 10 who is being monitored by an infrared spectroscopy unit 18 via a sensor unit 12 in accordance with the present invention, which is applied to the forehead of the patient 10 to optically access an internal tissue volume or regional field 14 within the cerebrum, directly adjacent the point where sensor 12 is located, but inside of the scalp, skull, and adjacent dura, i.e., within the brain tissue itself. The sensor unit 12 is coupled to the spectroscopy unit 18 through a conductor bundle 16 described more particularly hereinafter (shown in a bifurcated, divided form for purposes of illustration, although not actually implemented in this particular physical form in the preferred embodiment). As generally illustrated, the spectroscopy unit 18 includes a digital computer 20 having a monitor 22 on which visual displays may be perceived. It will be noted that the receiver (detector) conductor bundle portion 16a includes an amplification unit 24 disposed a short distance away from the patient 10, as described in more detail hereinafter.

Figure 3:
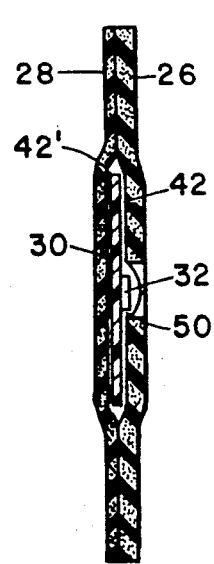
FIG. 3 is an enlarged cross-sectional end elevation taken along the plane III—III of FIG. 2.
Figure 4:
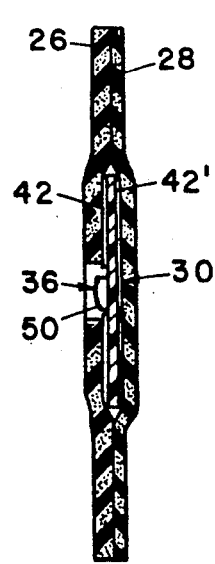
FIG. 4 is an enlarged cross-sectional end elevation taken along the plane IV—IV of FIG. 2.

The preferred embodiment of sensor 12 as described herein preferably comprises an elongated, somewhat rectangular member (FIG. 2) with rounded corners, from which the conductor bundle 16 extends outwardly. More particularly, sensor assembly 12 preferably comprises a laminar "sandwich" which includes an outer layer (i.e., a cover) having a softly resilient sheet of foam material 26 on the side facing the patient, and an outer backing layer 28 which may be of thinner material which is flexible but not necessarily resilient in character. The two layers 26, 28 are secured together adhesively, and between them is disposed an electrical component board 30 described in more detail hereinafter but adhesively secured in place as a unit so that electro-optical components carried thereon such as photodetectors 32, 34 and a light source 36 are disposed in registration with appropriate apertures 132, 134 and 136 formed in the foam layer 26 (FIGS. 3 and 4), through which such optical components may access the patient 10 (by emitting light which transmisses through the scalp, skull and brain tissue of region 14, and then detecting resultant light after it leaves such region and passes back out of the patient through the skull and scalp, etc.).

Figure 2:
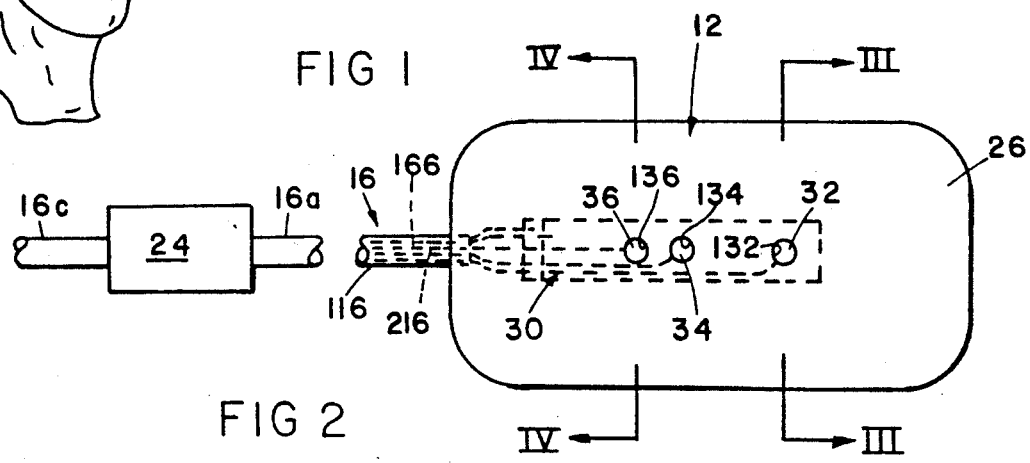
FIG. 2 is a side elevation of a preferred embodiment of the invention.
Figure 6:
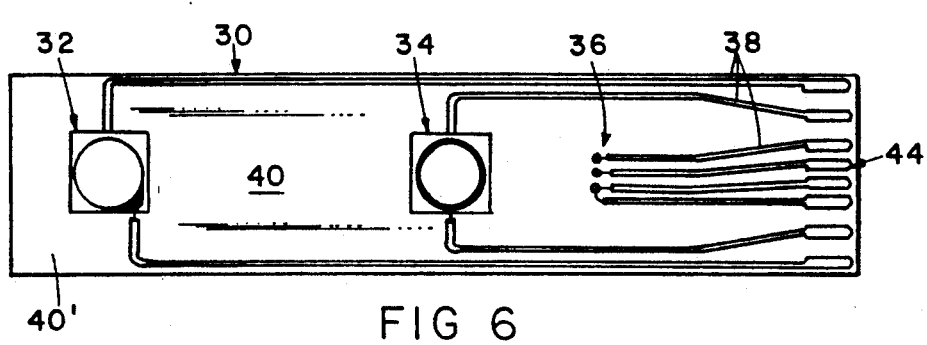
FIG. 6 is an enlarged side elevational view of the circuit board which carries the electro-optical components.

The electrical component board 30 is preferably much smaller in overall size than the outer dimensions of the foam layer and backing layer 26, 28 which provide the outwardly visible shape of sensor assembly 12 (as shown in FIG. 2), and preferably comprises a printed circuit board such as that illustrated in FIG. 6; more particularly, such "printed circuit" board 30 preferably comprises a flex circuit 40, having printed conductive strips 38 secured to one side of a stiffly flexible support strata 40' (FIG. 6). Support strata 40' integrally mounts the aforementioned photodetectors 32 and 34, as well as the light source 36 which are adhesively secured to the support strata and electrically connected to the respective strips 38 by a small wire-like conductor 39. In accordance with the preferred embodiment described herein, source 36 comprises a closely-grouped series of light-emitting diodes (L.E.D.'s) which are individually excited through particular ones of the strips 38, i.e., strips 38a, 38b and 38c (FIG. 7), in conjunction with a common ground conductor 38d. The conductive strips of flex circuit 40 are electrically connected to the adjacent portion 16a of conductor bundle 16 by soldering the end extremities of the electrical conductors (i.e. wires) 216 inside the conductor bundle 16a to the row of contacts 44 forming the end extremities of conductive strips 38, near one end of the board 30 (FIGS. 6 and 8).

Figure 7:
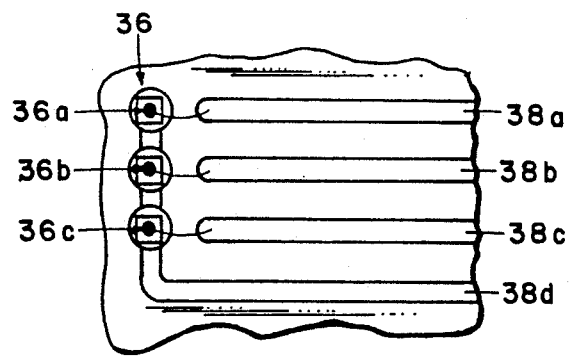
FIG. 7 is a fragmentary further enlarged view showing portions of the apparatus shown in FIG. 6.
Figure 8:
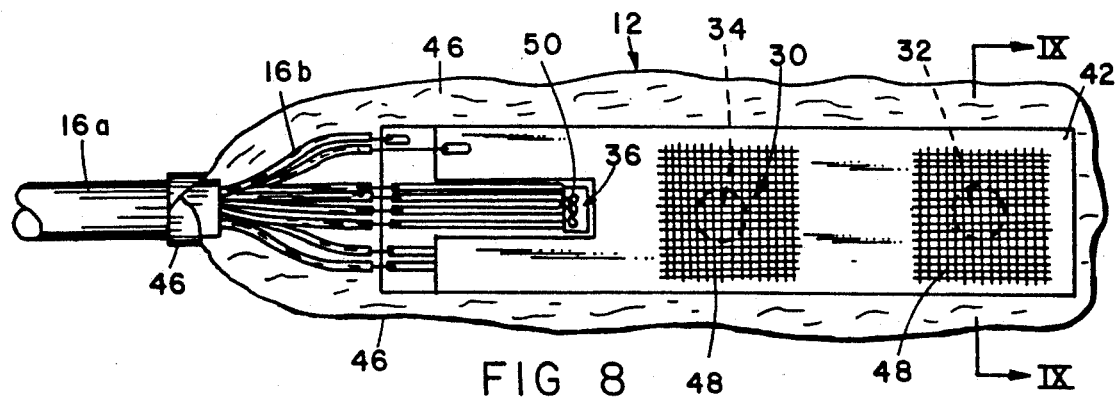
FIG. 8 is a fragmentary side elevational view showing a portion of the structure of FIG. 6 with certain of the shielding members in place and others partially removed.

As specifically shown in FIG. 7, there may be several different individual such L.E.D.'s, designated 36a, 36b, 36c, each for producing a specifically selected different light wavelength (as referred to in more detail in co-pending application Ser. No. 07/711,147. It is to be noted, in this connection, that it is also possible to implement the invention in other configurations, e.g., with remotely located light-producing elements and fiberoptic conductors and emitters; however, the preferred configuration illustrated provides certain advantages, particularly in conjunction with present-day L.E.D.s, which can provide surprising amounts of light intensity from a very small component with relatively low excitation. In one specific form presently contemplated as a best mode, the L.E.D.s 36 produce output intensities of about three milliwatts at ninety degree solid angle and require only about five volts d.c. excitation. The photodetectors 32, 34 preferably have sensitivities of about 500 milliamps/watt with peak spectral response at about 900-1000 nm, and are of the low noise type.

As explained at some length in the above-noted co-pending and incorporated applications (Ser. Nos. 329,945 and 07/711,149), the relative separation of (distance between) the light source 36 and the location of the detectors 32, 34 is of considerable importance to the particular purpose, function and application of the optical spectrophotometric device with which the sensor assembly 12 is to be used, since these distances effectively determine the location and size of the particular internal region 14 which is to be selectably examined by the interrogating light wavelengths. For the cerebral oximeter which is the subject of copending application Ser. No. 07/711,147, effective such distances are in the range of approximately 0.3 inches and 1.0 inches, respectively, and these distances thus constitute one particular selectively-determined preferred embodiment and best mode of the present invention; however, in the broader aspects of the underlying invention other and different such distances may be determined and specified without otherwise changing the overall nature of the apparatus and methodology (with the possible exception of specific component choices, since longer such distances may require other and different light intensities, etc. and other applications may require different interrogating wavelengths, etc.).

Figure 5:
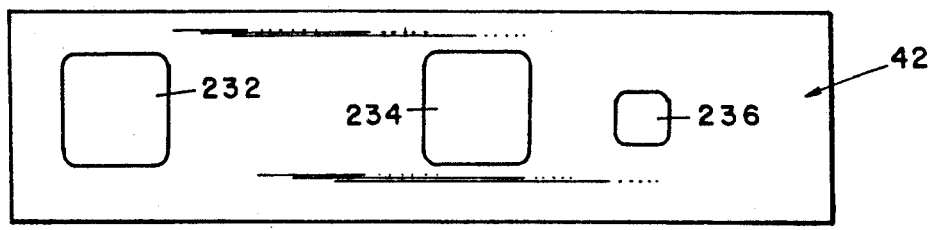
FIG. 5 is an enlarged side elevational view of a preferred form of shielding element for use in the apparatus.

In the preferred configuration referred to above and described herein, the electrical component board 30 is preferably covered on both major sides with a thin, stiffly flexible conductive metal layer such as that shown at 42 in FIG. 5, which adds a degree of structural support (i.e., strengthening of the flex circuit) but more importantly provides shielding against otherwise-disruptive or distorting influences such as electromagnetic or electrostatic fields as well as anomalous ambient light, etc. More particularly, layer 42 shown in FIG. 5 preferably comprises a thin sheet of copper which is of essentially the same outer dimensions as the flex circuit comprising board 30 in the preferred embodiment, and formed with apertures 232, 234 and 236 of a size and shape closely complementary to the outer periphery of the sensors 32 and 34, and the light source 36, i.e., the space immediately surrounding the L.E.D.s 36a, 36b, etc. Thus, layer 42 comprises in effect a mask which fits over the component side of board 30, and is preferably adhesively secured thereto (being electrically insulated from the conductors 38, etc. by the laminate structure of the flex circuit forming board 30, which includes a thin electrically insulating overlay). As already indicated, the opposite side of the flex circuit is also preferably covered by a shield layer 42' essentially similar to layer 42, although of course without the apertures since there are no electro-optical components on the reverse side of board 30. That is, the shielding and supportive layer 42' on the non-component side of flex circuit 40 is simply an imperforate sheet of the same conductive material as layer 42, adhesively secured in place.

Figure 9:
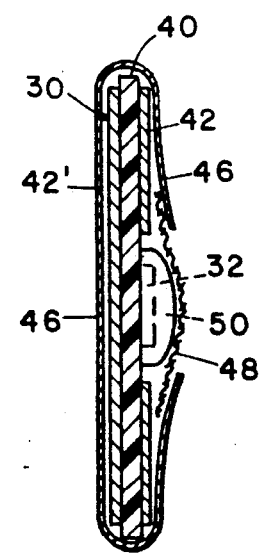
FIG. 9 is a cross-sectional end elevation taken along the plane IX—IX of FIG. 8.

The laminar "sandwich" described above which forms electrical component board 30 (including the flex circuit 40 together with its components and oppositely-disposed shielding layers 42, 42') is preferably additionally shielded by use of an overlay of conductive sheet material such as a foil-like metal, e.g., copper tape, as designated by the numeral 46 (FIG. 8), which is wrapped completely around the laminated "sandwich" on all sides except for closely-fitting apertures disposed in registration with apertures 232, 234 and 236 of mask layer 42 (FIG. 5). In addition, each of the electro-optical components (i.e., source 36 and detectors 32,34) preferably have a shield element 48 (FIGS. 8 and 9) in the form of conductive metal mesh or screen which is disposed directly over each of these elements (as a small patch) and which extends over the entire aperture 232, 234 and 236 of shield layer 42 (atop the aforementioned deposit of optically clear epoxy covering each electro-optical component), as well as under the adjacent edges of the registering apertures formed in the metal tape 46, to lie in electrical contact therewith. The foil-like (tape) shielding layer 46 is preferably secured in place by an electrically-conductive adhesive carried on one side, which integrates the tape into the composite shielding provided. To complete such shielding, conductor bundle 16a is preferably in the form of shielded "co-ax" cable, i.e., having a metallic mesh sleeve 16b (FIG. 2) which peripherally surrounds the electrical conductors 216 (which are mutually insulated from one another), and the sheath 16b (or an integral portion thereof) is extended toward and into contact with the outer shielding layer 42 (FIG. 8) of electrical component board 30, where it is soldered or otherwise secured in place. Sheath 16b is preferably disposed inside a generally tubular, rubber-like outer sleeve 116, which is preferably of an electrically insulating material and also serves esthetic purposes.

Accordingly, it will be appreciated that the electro-optical components, in particular detectors 32 and 34, are extensively shielded by the aforementioned layers 42, 42', 46, mesh patches 48, sheath 16b, etc., since the outer shielding tape layer 46 is also in electrical contact with sheath portion 16b, (through layer 42) and the sheath 16b extends outwardly to the amplifier unit 24, and into contact with a further ground conductor (not specifically shown) contained within conductor bundle 16c, that extends into the spectroscopy unit 18, and is connected to the system ground therewithin. This provides substantial protection against distortion for the comparatively low-level electrical signals produced by detectors 32 and 34 in response to receipt of the selected wavelengths of light from source 36 which have transmissed the region 14 being interrogated. This is an important aspect of the invention, since elimination of distortion, and thus enhanced signal-to-noise ratios, contribute significantly to the overall accuracy and success of the associated spectrophotometric apparatus and procedures. In this regard, the provision of the amplifier unit 24 at a selected distance away from the sensor 12 (e.g., at least about three feet, and preferably about five to six feet) is also a desirable aspect, since this helps to eliminate the presence of higher voltage or current levels at the sensor itself, close to the patient, while at the same time providing for minimal losses of signal between the patient and the spectroscopy unit 18. Of course, the particular attributes of the amplifier 24 should be selectively chosen to complement the electro-optical components as well as to provide the desired input levels for the spectroscopy unit. In addition, the amplifier 24 should be a low-noise device with high input impedance, such as the commercial amplifier unit known as the AD515 (Analog Devices). As will be appreciated by those skilled in art, the photodetectors 32, 34 are current-output devices, and as a result the resistivity of the conductors in cable portion 16a is of less significance. The output of amplifier 24, coupled to the spectroscopy unit 18, will be voltage-variant, however.

Further aspects of the preferred form of sensor assembly 12 in accordance with the invention include the following. It is important that the foam layer 26 be of black, light-absorbing material, in order to more effectively isolate ambient light from the electro-optical components 30, 32, 34, as well as to help prevent any possibility of surface leakage between source 36 and detectors 32, 34. This helps ensure that photons received by the detectors have actually transmissed the tissue of the patient, and thus carry desired information. In this connection, the surrounding apertures 132, 134 and 136 for the associated electro-optical components are preferably very closely-fitting (i.e., complementary) to the components, to further enhance such shielding effects. The rear layer 28, of the sensor assembly is preferably opaque to ambient light, i.e., is of dense and highly-reflective material (preferably being white in color) such as an imperforate sheet of polymeric material. In addition, the foam layer 26 is preferably of sufficiently open-celled character as to transmit water vapor from the patient, to prevent moisture build up between the outer face of foam layer 26 and the patient. One acceptable type of such material is polyurethane foam. As noted above, it is quite desirable to provide a small amount of an optically clear material such as epoxy over the light source 36, i.e., the grouped array of L.E.D.s 36a, 36b, etc. as well as over the photodetectors 32, 34, thereby further augmenting the retention of these elements in place atop the flex circuit 40 and, further, effectively filling the air gap which would otherwise exist between the outermost (top) surface of these components and the outer surface of the foam layer 26, where contact is made with the patient. Thus, the optically clear deposits 50 in effect provide low-loss light guides which actually make contact with the patient (particularly in view of the compressibility of the foam layer 26) to enhance the coupling of light into and out of the patient's tissue. In addition, the deposit over the source 36 somewhat modifies the resulting form of light emission from the L.E.D.s so that they less resemble a point source than would otherwise be true. That is, the desired form of light from source 36 is diffuse in nature, and of course is further diffused by the highly scattering effect of the brain or other tissue to be transmissed.

It is to be pointed out once again that while the foregoing disclosure addresses a particular preferred embodiment, and best mode, the apparatus in accordance with the invention, and that the various recited detailed aspects thereof are regarded as being important to the most preferred version of the particular sensor described herein to illustrate the principles and concepts involved in the invention, other embodiments and versions of the invention may well be appropriate in other circumstances. It is therefore to be understood that the foregoing description of a particular preferred embodiment is provided for purposes of description and illustration, and not as a measure of the invention, whose scope is to be defined solely by reference to the ensuing claims. Embodiments of the invention differing from those set forth above which nonetheless utilize the underlying concepts of the invention and incorporate its spirit should therefore be considered as within the scope of the claims appended below, unless such claims by their language specifically state otherwise.

The embodiments of the invention in which an exclusive property or privilege is claimed are defined as follows:

1. An optical sensor unit for use as a patient interface device in conducting in vivo spectrophotometric examination procedures, comprising in combination: a body having at least limited longitudinal flexibility and a softly resilient outer cover carried on at least one side, for comfortably and contiguously contacting a selected surface area on a patient; an electro-optical light source carried with said body and exposed through said resilient cover, for emitting light of at least two selected wavelengths and introducing such light into said patient through said surface area; a plurality of electro-optical light detectors carried with said body and maintained at particular spacings from one another and from said light source thereby, said detectors being exposed through said resilient cover to receive light from said patient resulting from said introduced light from said light source; electrical conductors coupled to said light source and light detectors to energize said source and to convey output signals from said detectors representative of the resultant light received from said patent, said conductors extending outwardly from said body for coupling to a remotely located signal-processing device; said resilient cover comprising a thin, softly compressible member of light-absorbing and moisture-transmissible material which helps isolate said source from said detectors with respect to light traveling directly therebetween as well as from ambient light while also acting to convey moisture away from said patient surface area, to enhance the fidelity and accuracy of said detector output signals.

2. The optical sensor unit as recited in claim 1, further including means for shielding said light detectors and at least portions of their said electrical conductors from ambient sources of electrical noise and/or like distortion, to help maintain the fidelity of said signals to the detected representative light; said shielding means including at least one thin layer of lightly flexible and longitudinally resilient, electrically conductive sheet metal, said layer overlying said body throughout the portion thereof carrying said detectors to provide a shielding for them and the immediately adjacent electrical conductors to which they are directly coupled; wherein said thin layer of said sheet metal is disposed on the inside of said body and extends alongside at least portions of said detectors.

3. The optical sensor unit as recited in claim 2, wherein said means for shielding further includes a sheath substantially surrounding at least portions of said conductors extending outward beyond said body.

4. The optical sensor unit as recited in claim 3, wherein said thin sheet member is electrically coupled to said sheath.

5. The optical sensor unit as recited in claim 2, wherein said body includes a circuit board underlying and supporting said detectors, said circuit board comprising a generally planar member carrying electrically-conductive strips comprising at least in part said conductors coupled to said detectors, said thin sheet metal shielding member overlying at least portions of said circuit board adjacent said detectors.

6. The optical sensor unit as recited in claim 5, wherein said means for shielding includes a thin sheet-like member which substantially envelopes said circuit board and is disposed in juxtaposition to at least portions of said detectors.

7. The optical sensor unit as recited in claim 6, wherein said thin sheet-like shielding member overlies the side of said circuit board carrying said detectors and is apertured to expose the latter for operation.

8. The optical sensor unit as recited in claim 5, wherein said thin sheet member is substantially coextensive with and overlies said circuit board and said conductive strips.

9. The optical sensor unit as recited in claim 8, wherein said means for shielding further includes a sheath surrounding at least portions of said conductors extending outwardly from said body, and wherein said thin sheet member is electrically coupled to said sheath.

10. The optical sensor unit as recited in claim 5, wherein said shielding means comprises a sheet of conductive foil wrapped about and substantially enveloping said circuit board and its conductor strips.

11. The optical sensor unit as recited in claim 1, wherein said light detectors comprise photodiodes having a sensitivity on the order of about 500 milliamps per watt, and are of a low-noise type.

12. The optical sensor unit as recited in claim 1, wherein said light source comprises at least one L.E.D. having an output on the order of about three milliwatts and an output light solid angle of about ninety degrees.

13. The optical sensor unit as recited in claim 1, wherein said amplifier unit is located at least three feet away from said electro-optical light source and detectors.

14. The optical sensor unit as recited in claim 1, wherein said source and said detectors comprise low-power components requiring only low levels of current and voltage essentially negligible to human comfort and safety; and electric signal amplification means coupled to receive said output signals from said light detectors via their said electrical conductors for amplification of said signals prior to processing thereof, said amplification means comprising an amplifier unit which is physically located between said patient and said signal-processing device, to protect said patient from higher power levels.

15. The optical sensor unit as recited in claim 1, wherein said body further includes a flexible sheet disposed on the rearward side thereof opposite the cover contacting said patient, to sandwich at least portions of said electro-optical source and detectors therebetween, said sheet being of light-reflective material and generally opaque in nature to further isolate said source and detectors from ambient light.

16. The optical sensor unit as recited in claim 1, wherein said cover comprises a resilient foam material having vapor-transmissive characteristics.

17. The optical sender-receiver unit as recited in claim 16, wherein said foam is of open-cell form.

18. The optical sender-receiver unit as recited in claim 16, wherein said foam is black in color and highly light-absorbing.

* * * * *